(12) United States Patent
Alferness et al.

(10) Patent No.: US 8,114,064 B2
(45) Date of Patent: Feb. 14, 2012

(54) INFUSION DEVICE WITH PISTON PUMP

(75) Inventors: Clifton A. Alferness, Port Orchard, WA (US); John M. Adams, Kirkland, WA (US); Daniel Hawkins, Newcastle, WA (US)

(73) Assignee: Calibra Medical, Inc., Redwood City, CA (US)

( * ) Notice: Subject to any disclaimer, the term of this patent is extended or adjusted under 35 U.S.C. 154(b) by 474 days.

(21) Appl. No.: 11/705,812

(22) Filed: Feb. 12, 2007

(65) Prior Publication Data

US 2007/0299401 A1     Dec. 27, 2007

Related U.S. Application Data

(60) Provisional application No. 60/782,941, filed on Mar. 16, 2006.

(51) Int. Cl.
*A61K 9/22* (2006.01)
*A61M 5/20* (2006.01)
*A61M 1/00* (2006.01)

(52) U.S. Cl. .................. 604/890.1; 604/131; 604/141; 604/151

(58) Field of Classification Search ............... 604/891.1, 604/143, 151
See application file for complete search history.

(56) References Cited

U.S. PATENT DOCUMENTS

| | | | |
|---|---|---|---|
| 4,263,909 A | 4/1981 | Bush | |
| 4,360,019 A * | 11/1982 | Portner et al. | 604/131 |
| 4,643,723 A * | 2/1987 | Smit | 604/207 |
| 4,681,560 A * | 7/1987 | Schulte et al. | 604/9 |
| 4,705,464 A * | 11/1987 | Arimond | 417/477.7 |
| 4,773,900 A * | 9/1988 | Cochran | 604/143 |
| 4,850,955 A | 7/1989 | Newkirk | |
| 5,061,243 A * | 10/1991 | Winchell et al. | 604/132 |
| 5,230,706 A * | 7/1993 | Duquette | 604/83 |
| 5,545,143 A | 8/1996 | Fischell | |
| 5,752,930 A | 5/1998 | Rise et al. | |
| 5,785,688 A * | 7/1998 | Joshi et al. | 604/141 |
| 6,200,055 B1 * | 3/2001 | Fusaro, Jr. | 401/178 |
| 6,270,481 B1 | 8/2001 | Mason et al. | |
| 6,497,680 B1 * | 12/2002 | Holst et al. | 604/153 |
| 6,719,728 B2 * | 4/2004 | Mason et al. | 604/181 |
| 7,201,746 B2 * | 4/2007 | Olsen | 604/891.1 |
| 7,255,690 B2 * | 8/2007 | Gray et al. | 604/891.1 |
| 2003/0088238 A1* | 5/2003 | Poulsen et al. | 604/890.1 |
| 2003/0229310 A1* | 12/2003 | Flaherty et al. | 604/151 |
| 2004/0092865 A1* | 5/2004 | Flaherty et al. | 604/93.01 |

(Continued)

FOREIGN PATENT DOCUMENTS

EP         0941741        9/1999

(Continued)

OTHER PUBLICATIONS

Young, PCT International Search Report, Apr. 14, 2008.

*Primary Examiner* — Nicholas D Lucchesi
*Assistant Examiner* — Ian Holloway
(74) *Attorney, Agent, or Firm* — Richard O. Gray, Jr.; Graybeal Jackson LLP

(57) ABSTRACT

A disposable infusion device comprises a base, a cannula arranged to extend from the base to beneath the patient's skin to deliver a liquid medicament to the patient, and a source arranged to provide the cannula with a liquid medicament. The source comprises a piston pump.

1 Claim, 6 Drawing Sheets

U.S. PATENT DOCUMENTS

| | | | |
|---|---|---|---|
| 2006/0069382 A1* | 3/2006 | Pedersen | 604/890.1 |
| 2006/0184121 A1* | 8/2006 | Brockman et al. | 604/151 |
| 2006/0264835 A1* | 11/2006 | Nielsen et al. | 604/174 |
| 2010/0198183 A1* | 8/2010 | Lanigan et al. | 604/406 |
| 2010/0232992 A1* | 9/2010 | Gray | 417/417 |

FOREIGN PATENT DOCUMENTS

| | | |
|---|---|---|
| WO | 2005039673 A2 | 5/2005 |

* cited by examiner

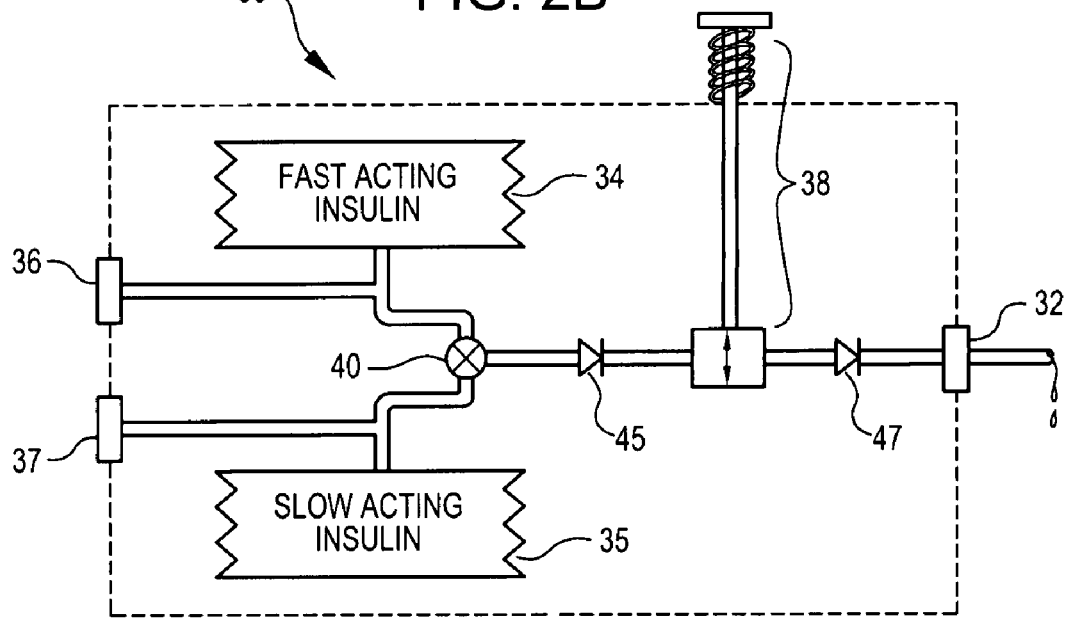
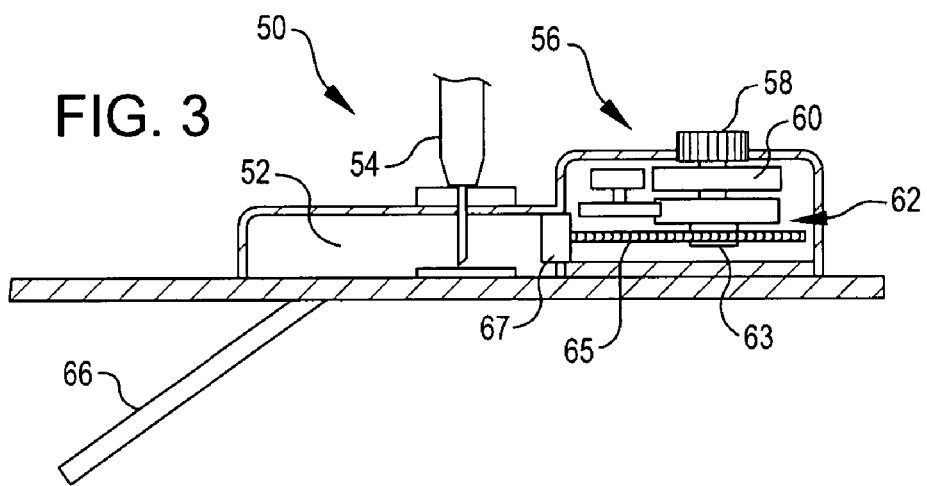

INFUSION DEVICE WITH PISTON PUMP

CLAIM OF PRIORITY

This application claims priority to U.S. Provisional Application Ser. No. 60/782,941, filed on Mar. 16, 2006, which is incorporated by reference.

BACKGROUND

Tight control over the delivery of insulin in both type I (usually juvenile onset) and type II (usually late adult onset), has been shown to improve the quality of life as well as the general health of these patients. Insulin delivery has been dominated by subcutaneous injections of both long acting insulin to cover the basal needs of the patient and by short acting insulin to compensate for meals and snacks. Recently, the development of electronic, external insulin infusion pumps has allowed the continuous infusion of fast acting insulin for the maintenance of the basal needs as well as the compensatory doses for meals and snacks. These infusion systems have shown to improve control of blood glucose levels, however, they suffer the drawbacks of size, cost, and complexity, which prevents many patients from accepting this technology over the standard subcutaneous injections. These pumps are electronically controlled and must be programmed to supply the desired amounts of basal and bolus insulin.

SUMMARY

In one embodiment of the invention, a disposable infusion device comprises a base, a cannula arranged to extend from the base to beneath the patient's skin to deliver a liquid medicament to the patient, and a source arranged to provide the cannula with a liquid medicament, the source comprising a piston pump.

The base may be arranged to adhere to a patient's skin. The piston pump is preferably a fixed stroke piston pump.

The source may include a reservoir for holding the liquid medicament and the piston pump may be arranged for pumping the liquid medicament from the reservoir to the cannula. The device may further comprise a one way valve between the reservoir and the piston pump. The device may further comprise a one way valve between the piston pump and the cannula.

The device may further comprise a port communicating with the reservoir to receive the liquid medicament from an instrument external to the device to fill the reservoir.

In another embodiment, a disposable infusion device comprises a base adapted to adhere to a patient's skin, a cannula arranged to extend from the base to beneath the patient's skin to deliver a liquid medicament to the patient, a reservoir for containing the liquid medicament, and a piston pump that pumps the liquid medicament from the reservoir to the cannula.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 2B a schematic diagram illustrating another potential manner of operation of the system of FIG. 2;

FIG. 3 is a side view, with portions cut away, of a disposable insulin infusion system including a mechanical timer according to another embodiment of the invention;

DETAILED DESCRIPTION

Figure 1:
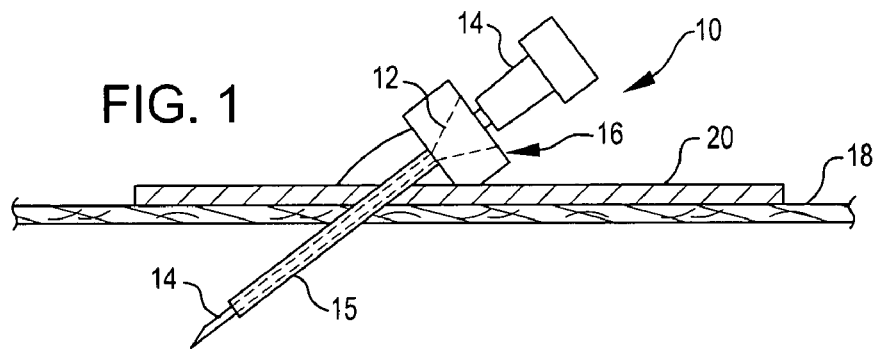
FIG. 1 is a side view of an infusion port that may be used in practicing the invention.

FIG. 1 shows an infusion port 10 into which a liquid medicament, such as insulin or incretins, can be injected manually using a standard syringe. The port 10 includes a funnel port 12, an insertion needle 14, and an injection membrane 16. The port 10 may be adhered to the skin 18 with adhesive tape 20. This system obviates the need for multiple daily percutaneous needle sticks to accomplish the provision of insulin dosage.

The port 10 further includes a cannula 15. The cannula 15 is carried by the funnel port 12. As known in the art, once the needle 14 and cannula 15 are positioned beneath the skin 18 as shown, the needle 14 is removed leaving the cannula 15 in a deployed position and ready to deliver insulin to the patient.

Figure 2:
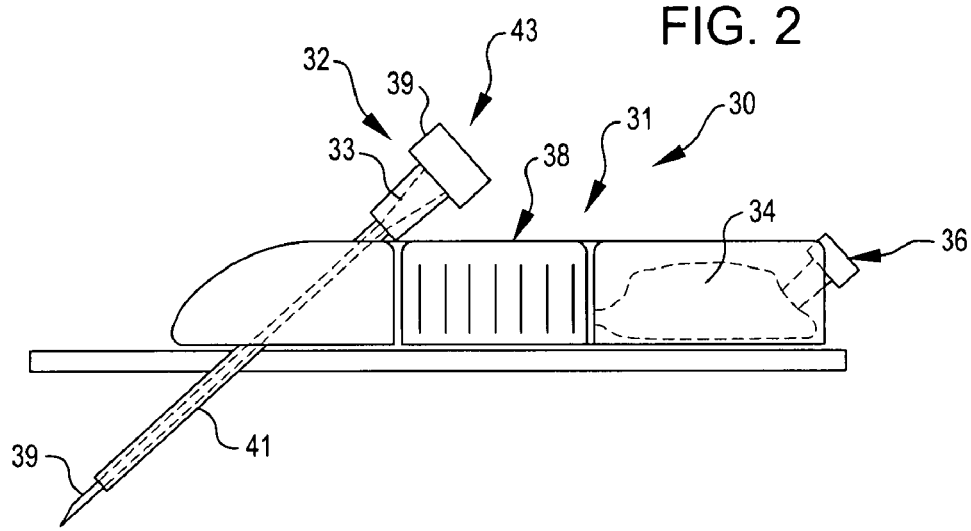
FIG. 2 is a side view of an infusion port, loading membrane, and insulin reservoir according to one embodiment of the invention.

FIG. 2 shows a system 30 according to one embodiment of the invention. The system includes an infusion port 32 similar to port 10 for delivery of either long acting or short acting insulin. The port 32 is shown prior to the needle 39 being withdrawn from the cannula 41. The system includes a first source 31 including a reservoir 34 which may be filled with a fast acting insulin through a port 36 and a pump 38. A further reservoir may be provided as will be seen subsequently. The port allows for reservoir 34 to internally hold a first liquid medicament, such as a fast acting insulin, for delivery at meals, for example, while the funnel port 33 of the port 32 forms a second source 43 and allows for a second liquid medicament, such as a slow acting insulin to be delivered as, for example, in the morning after awakening. The fast acting insulin may be delivered by the pump 38 which may be squeezed with the fingers.

In the case when the system 30 includes multiple reservoirs, the system may have a mechanism for the selection of which insulin is infused at any given time. It also may provide control over how much of each particular insulin is determined to be delivered by having the patient depress the actuator 38 a desired number of times. For example, each activation might deliver 0.5 units of insulin. Therefore, if 3 units of insulin are desired, 6 depressions will deliver the desired amount.

Figure 2A:
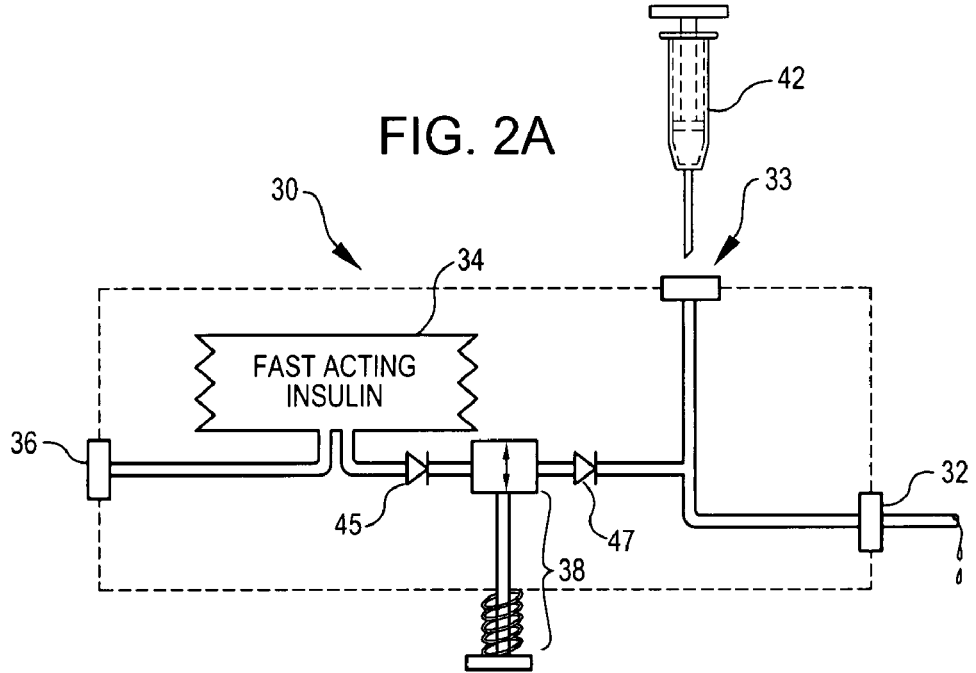
FIG. 2A is a schematic diagram illustrating one potential manner of operation of the system of FIG. 2.

FIG. 2A shows one manner of operation of the system 30. Fast acting insulin may be loaded into reservoir 34 through loading port 36. The pump 38 may be a piston pump and more particularly, a fixed stroke piston pump which provides a predetermined volume of insulin upon each actuation. The number of depressions of pump 38 thus determines the amount of the fast acting insulin delivered from reservoir 34 to port 32 and cannula 41. When a slow acting insulin is to be delivered, such as in the morning upon awakening, the slow acting insulin may be delivered through funnel port 33. In that regard, it will be noted that the port 33 permits the slow acting insulin to be received from an instrument, such as syringe 39, from external to the system 30. It may further be noted that the infusion system 30 further includes one-way valves 45 and 47. Valve 45 is between the pump 38 and reservoir 34 and valve 47 is between port 32 and pump 38.

FIG. 2B shows another manner in which the system 30 may operate. Here, in addition to the reservoir 34 for the fast acting insulin, the system includes another reservoir 35 to contain slow acting insulin. The fast acting insulin is loaded into reservoir 34 through port 36. The slow acting insulin may be loaded into the reservoir 35 through port 37. A valve 40 controls which reservoir is selected as well as the rate in which the selected insulin is delivered. The pump 38, which again may be a fixed stroke piston pump, is used for pumping the selected insulin out to the patient through port 32. Valves 45 and 47 remain on opposite sides of the pump 38.

FIG. 3 shows a system 50 for the constant delivery of a fixed amount of insulin per unit time. The insulin delivered over time is fast acting insulin, to meet the basal needs. This insulin is contained in a reservoir 52. An adjunctive port 54 for the injection of fast acting insulin for meals and snacks is also provided.

The insulin in reservoir 52 is constantly delivered under the control of a mechanical timer pump 56. The timer pump is of the type known in the art to include a winder 58, a wind-up spring 60, and gears 62. The gears 62 drive a worn gear 63 and lead screw 65 to drive a piston 67. The piston 67 thus pressurizes the reservoir 52 to provide a constant flow of insulin to the cannula 66. When a bolus of fast acting insulin is required, such as at meals, the port 54 is used to inject the fast acting insulin into the reservoir 52. When the reservoir is full, further injected insulin will displace a like quantity of insulin from reservoir 52 thereby injecting the same into and out of the cannula 66.

Figure 4:
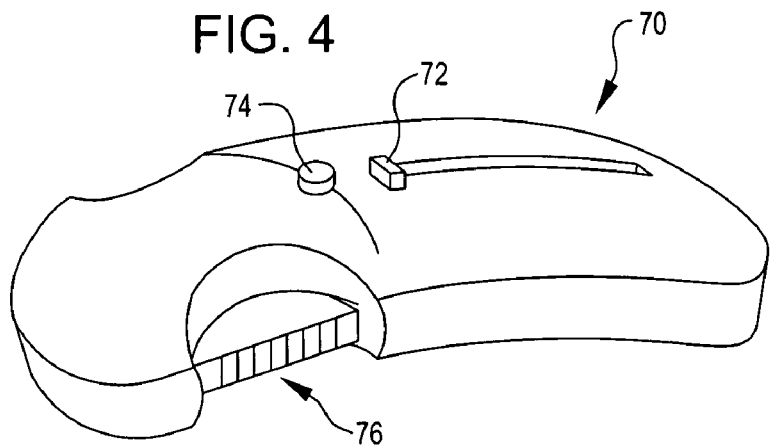
FIG. 4 is a perspective view of a disposable insulin infusion system that provides for both basal delivery and bolus delivery of insulin according to an embodiment of the invention.

FIG. 4 shows a device embodiment 70 with an infusion port for the delivery of a fixed amount of fast acting insulin per unit time plus the mechanisms for delivery of boluses for meals and snacks. A slide 72 is provided to pressurize the insulin chamber (not shown). A filling membrane 74 permits the chamber to be filled. A trigger 76 may be depressed for each measured bolus of insulin to be delivered.

Figure 4A:
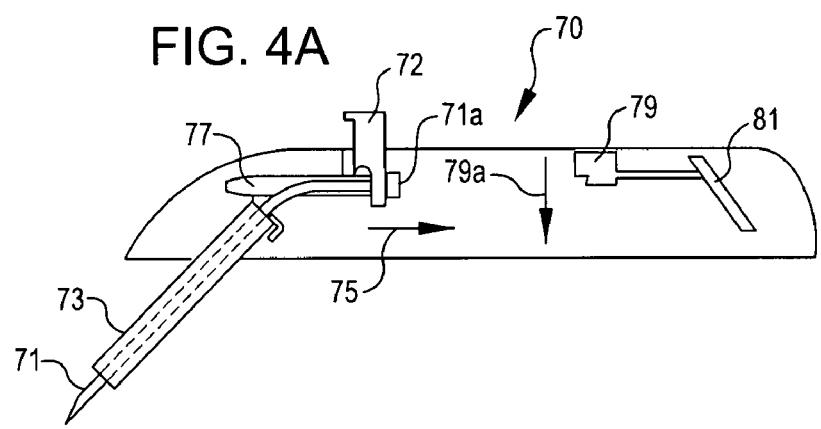
FIG. 4A is a side view, with portions cut away, showing more particulars of the operation of the system of FIG. 4.

Referring now to FIG. 4A, here it may be seen that the slide 72 performs an additional function after the patient has deployed the cannula 73. More specifically, the needle 71 may be retracted from the cannula 73 to leave the cannula 73 in a fully deployed position for delivering insulin to the patient. To this end, the slide 72 is coupled to the device needle 71 housed in the infusion tube 73. As the slide is slid back in the direction of the arrow 75, the needle 71 is retracted. Eventually, the needle is captured by a needle capture chamber 77. Further backward movement of slide 72 eventually causes the needle head 71a to be caught by a needle ejector 79. Upon further backward movement of slide 72, the needle ejector 79 is acted upon by a ramp 81 that causes the needle head to be displaced in the direction of arrow 79a. Such needle head displacement forces the needle off of the slide 72. At this point, the needle is dropped within the device 70 and cannot be reused. The device is now safe and ready for disposal after it has been fully used.

Figure 5:
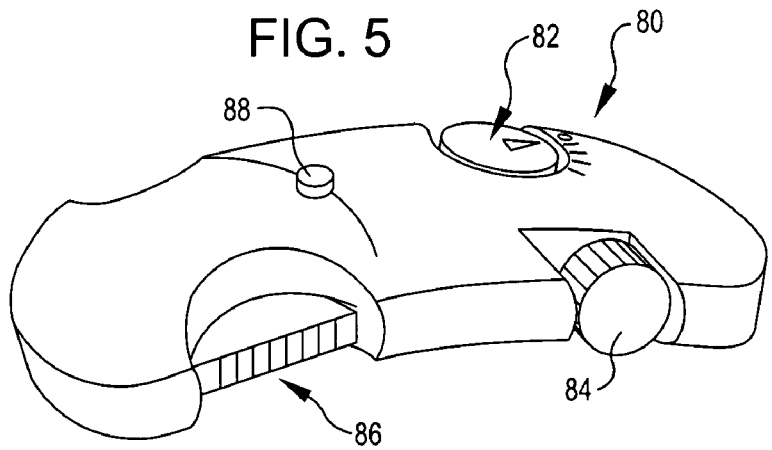
FIG. 5 is a perspective view of a disposable insulin infusion system providing user basal delivery rate adjustment and bolus delivery of insulin.

FIG. 5 shows a similar device 80 having a dial for the delivery of a user adjusted variable amount of fast acting insulin per unit time. This embodiment is particularly helpful for patients who may need a different amount of basal insulin support at different times during the day. The device 80 further includes mechanisms including a wind-up 84 and trigger 86 for delivery of boluses for meals and snacks. A filling membrane 88 is provided to facilitate filling of the insulin reservoir (not shown) with the fast acting insulin.

Figure 6:
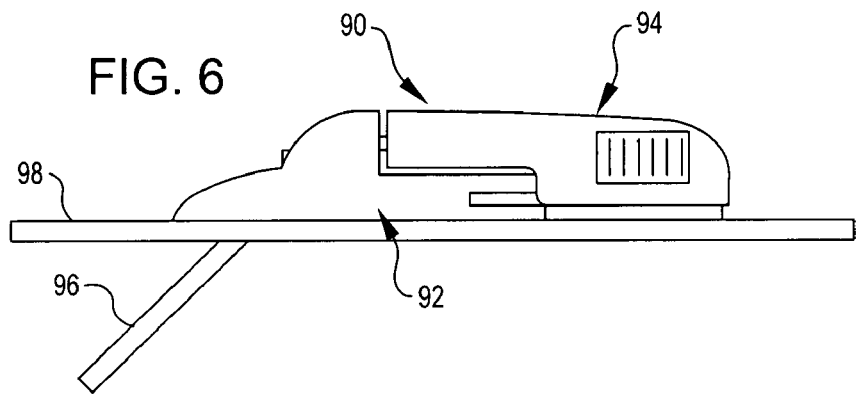
FIG. 6 is a side view of a disposable insulin infusion system including constant insulin delivery device and a separate mating bolus delivery device according to an embodiment of the invention.

FIG. 6 shows an embodiment of infusion port 90 with an internal reservoir 92 to hold fast acting insulin for constant delivery of a fixed amount per unit time to meet the basal needs of the patient with an adjunctive bolus module 94 to provide separate bolus delivery. The module 94 is mated to the internal reservoir for the needs of meals and snacks. The module 94 may contain enough insulin to last considerably longer than the insulin contained in the reservoir 92. When reservoir 92 is exhausted, the module 94 may simply be mated with another reservoir like that of reservoir 92. Both the constantly fed insulin and the boluses may be delivered through the infusion tube 96. The device may be adhered to the skin with adhesive tape 98.

Figure 7:
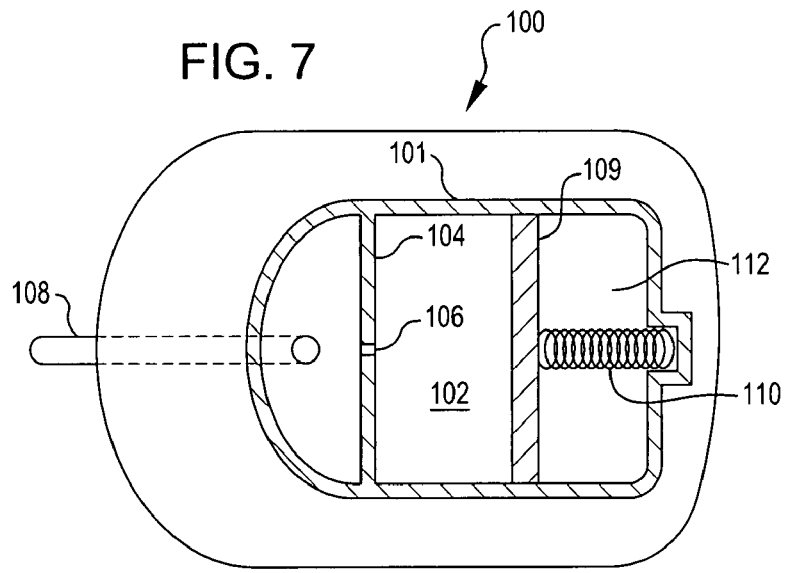
FIG. 7 is a top view, with portions cut away, of an insulin infusion system according to another embodiment of the invention having insulin delivery rate determined by a chamber pressure.

FIG. 7 shows a disposable insulin infusion device 100 for delivery of a constant flow of insulin utilizing a substantially constant pressure source and a small, flow control orifice. More specifically, the device 100 includes a reservoir 101 including a chamber 102 for containing a fast acting insulin. A wall 104 of the chamber 102 includes a small orifice 106. Another wall 109 of the chamber 102 is moveable under the influence of a spring 110 within an expanding chamber 112. This pressurizes the reservoir 102 to control the flow of insulin through the orifice 106 and into the infusion tube or cannula 108. Hence, the device 100 of FIG. 7 is similar to the device of FIG. 3 in that a reservoir of insulin is pressurized to deliver a constant flow of insulin to a cannula.

Figure 7A:
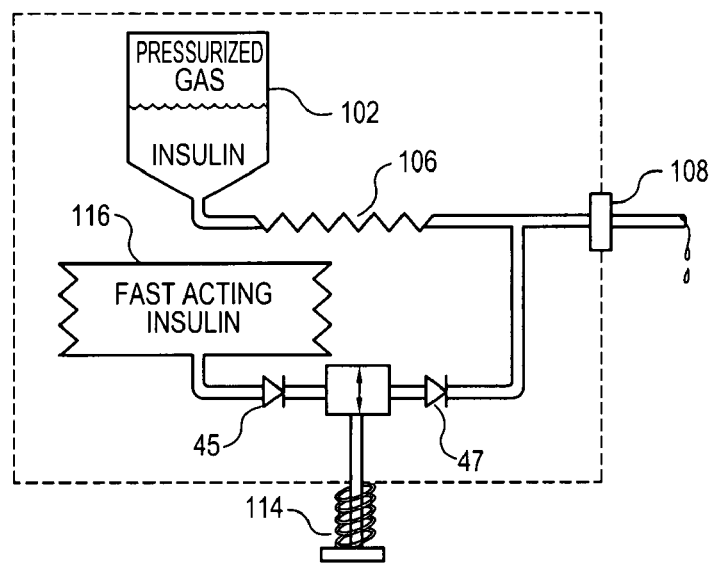
FIG. 7A is a schematic diagram illustrating one potential manner of operation of the system of FIG. 7.

FIG. 7A is a schematic representation of the operation of another device 115 similar to the device 100 of FIG. 7. Here it may be seen that the insulin is pressurized by gas within the pressurized reservoir 102. The orifice 106 restricts the flow of insulin by a controlled amount to the infusion tube or cannula 108. In addition, the device 115 includes a bolus pump 114 to pump boluses of fast acting insulin from another reservoir (or the same reservoir) to the infusion tube or cannula 108. Again, the pump 114 may be a fixed stroke piston pump. Also, one-way valves 45 and 47 are positioned on opposite sides of the pump 114 as in previous embodiments.

Figure 8:
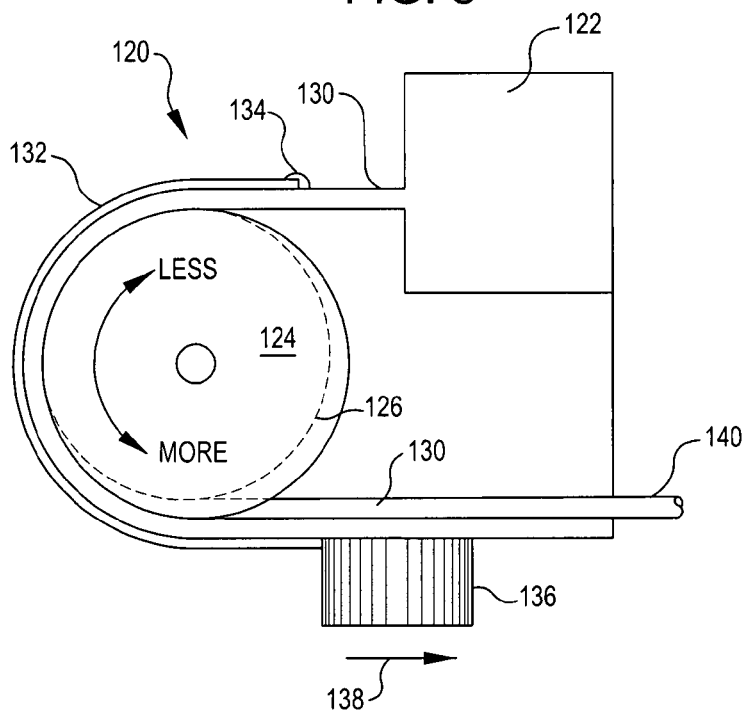
FIG. 8 is a side view of an insulin infusion system having insulin bolus delivery volume controlled by peristaltic action according to an embodiment of the invention.
Figure 9:
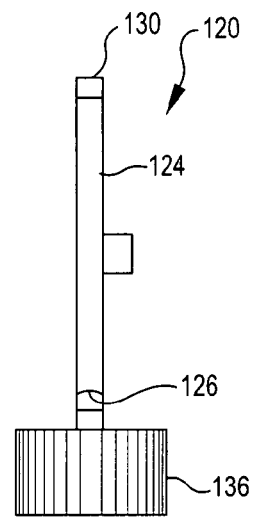
FIG. 9 is an end view of the system of FIG. 8.

FIGS. 8 and 9 show another disposable insulin infusion device 120 embodying the invention. Here, a volume adjustment mechanism is provided to control the volume of insulin delivered with each actuation. This actuation may be manual to adjust boluses for meals and snacks or at specific timed intervals for an adjustable effective basal rate.

More specifically, the device 120 includes a reservoir 122 for containing a fast acting insulin. The device further includes disk 124 having a groove 126 that increases in depth along the circumference of the disk 124. A flexible tube 130 extends from the reservoir 122 around the disk 124 and within the groove 126. A strap 132 extends from a fixed tie point 134 along the tube 130 to an actuator 136. As the disk is rotated in the clockwise direction, an increasing length of the tube 130 will reside in the groove 126. Conversely, counter-clockwise rotation of disk 124 will cause a decreased length of the tube 130 to reside in the groove 126. When the actuator 136 is moved in the direction of arrow 138, the strap 132 acts upon (compresses) the portion of the tube 130 not in the groove 126 to cause a measured bolus of insulin to be delivered to the infusion tube 140. Hence, as more tubing is acted upon by the strap 132, a larger volume bolus is delivered by peristaltic action. The disk 124 may be rotated by a dial, such as the dial 82 of the device 86 of FIG. 5.

Figure 10:
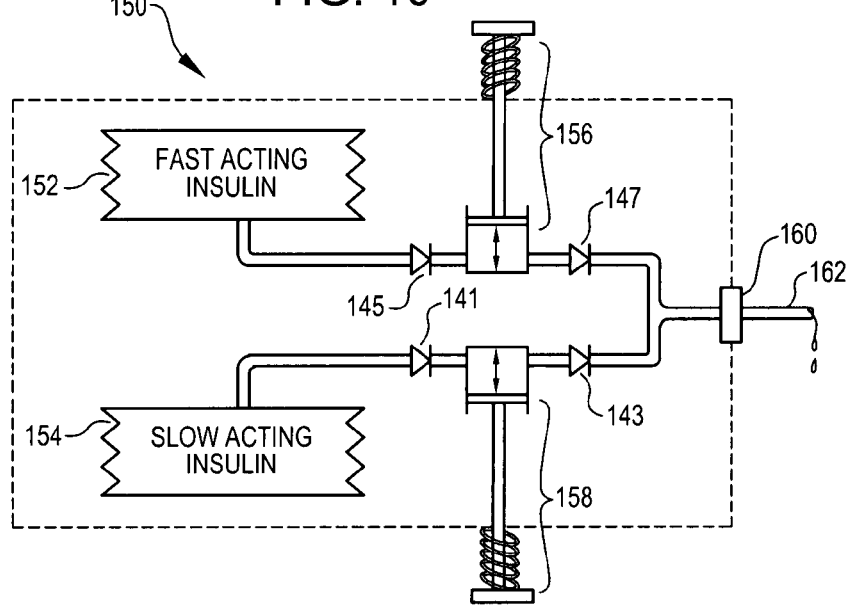
FIG. 10 is a schematic diagram of a further system embodying the invention.

FIG. 10 schematically illustrates the operation of another disposable insulin infusion device 150 embodying the invention. Here there are separate reservoirs 152 and 154 for fast acting insulin and slow acting insulin respectively. Each reservoir is associated with its own respective pump. Reservoir 152 is associated with pump 156 and reservoir 154 is associated with pump 158. The pumps 156 and 158 may be fixed stroke piston pumps as shown. The reservoirs 152 and 154 deliver under the pumping action of pumps 156 and 158 their respective insulin to a common port 160 coupled to a cannula 162. Again, one-way valves 145 and 147 are on opposite sides of pump 156, and one-way valves 141 and 143 are on opposite sides of pump 158.

Figure 11:
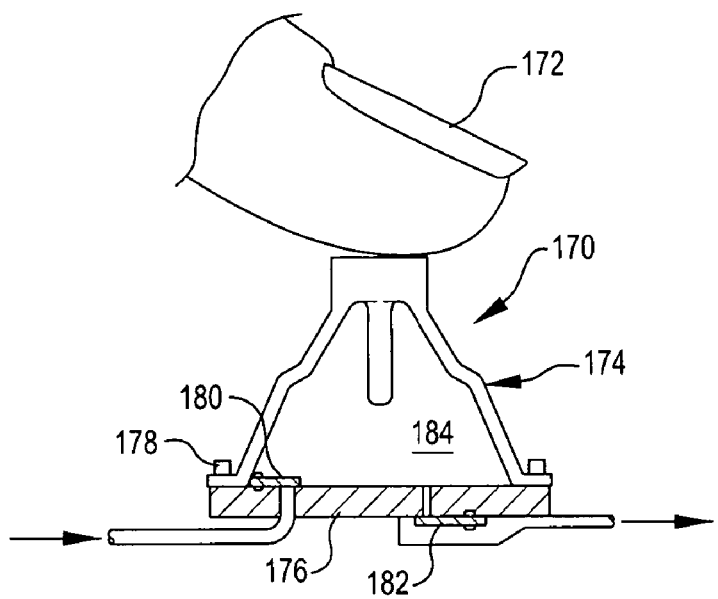
FIG. 11 is a side view, with portions cut away, of a bolus pump embodying the invention prior to insulin delivery.
Figure 12:
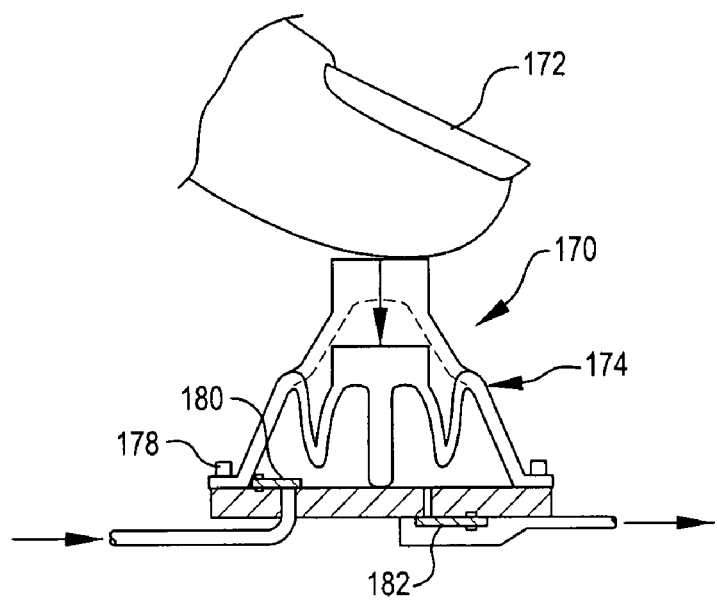
FIG. 12 is a side view, with portions cut away, of the bolus pump of FIG. 11 embodying the invention after insulin delivery.

FIGS. 11 and 12 show a bolus pump 170 embodying the invention. The pump 170 takes the form of a dome pump as illustrated. FIG. 11 shows the pump 170 prior to being depressed by the patient's finger 172 and FIG. 12 shows the pump after being depressed and insulin delivery. The pump 170 may be arranged to deliver 0.5 units of insulin with each actuation and provide tactile feedback with each actuation of the pump.

As may be noted, the pump includes a resilient membrane 174 sealed to a base 176 by a sealing ring 178. The base may be adhered to the patient's skin by adhesive tape (not shown). The pump 170 also includes an intake valve 180 which permits insulin to enter the inner cavity 184 formed by the membrane 174 and base 176 when the membrane returns to the configuration shown in FIG. 11. An output valve 182 permits insulin to flow from the cavity 184 when the membrane is depressed as shown in FIG. 12. The inner cavity may be arranged to displace a volume of 0.5 units of insulin for each depression of the pump 170. Hence, if 3 units of insulin are required for a meal, for example, the pump 170 may be depressed 6 times to deliver the desired amount of insulin to the patient.

While particular embodiments of the present invention have been shown and described, modifications may be made, and it is therefore intended in the appended claims to cover all such changes and modifications which fall within the true spirit and scope of the invention as defined by those claims.

What is claimed is:

1. A disposable infusion device comprising:
   a base arranged to adhere to a patient's skin;
   a cannula arranged to extend through the base to beneath the patient's skin to deliver a liquid medicament to the patient;
   a source arranged to provide the cannula with a liquid medicament, the source including a fixed volume piston pump including a piston and a piston chamber arranged to provide, with each actuation of the piston, the fixed volume of medicament from the piston chamber to the cannula; and
   an actuator directly connected to the piston of the piston pump and being manually displaceable to in turn directly displace the piston into the piston chamber of the piston pump to deliver the fixed volume of medicament from the piston chamber to the cannula.

\* \* \* \* \*